US009445765B2

(12) United States Patent
Banet et al.

(10) Patent No.: US 9,445,765 B2
(45) Date of Patent: Sep. 20, 2016

(54) INTERNET-BASED SYSTEM FOR CHARACTERIZING PATIENTS UNDERGOING AN ELECTROPHYSIOLOGY PROCEDURE

(71) Applicant: TOSENSE, INC., La Jolla, CA (US)

(72) Inventors: Matthew Banet, San Diego, CA (US); Gregory Feld, Rancho Santa Fe, CA (US); Andrew Terry, San Jose, CA (US)

(73) Assignee: TOSENSE, INC., La Jolla, CA (US)

(*) Notice: Subject to any disclaimer, the term of this patent is extended or adjusted under 35 U.S.C. 154(b) by 0 days.

(21) Appl. No.: 13/951,342

(22) Filed: Jul. 25, 2013

(65) Prior Publication Data

US 2014/0039334 A1 Feb. 6, 2014

Related U.S. Application Data

(60) Provisional application No. 61/675,752, filed on Jul. 25, 2012.

(51) Int. Cl.
*A61B 5/04* (2006.01)
*A61B 5/00* (2006.01)
*A61B 5/0245* (2006.01)
*A61B 5/0452* (2006.01)
*A61B 5/044* (2006.01)
*A61B 5/0205* (2006.01)

(52) U.S. Cl.
CPC .......... *A61B 5/4848* (2013.01); *A61B 5/0006* (2013.01); *A61B 5/0022* (2013.01); *A61B 5/0205* (2013.01); *A61B 5/0245* (2013.01); *A61B 5/044* (2013.01); *A61B 5/04012* (2013.01); *A61B 5/0452* (2013.01); *A61B 5/686* (2013.01); *A61B 5/7475* (2013.01)

(58) Field of Classification Search
CPC ........... A61B 5/04085; A61B 5/0022; A61B 5/0468; A61B 5/04012; A61B 5/0205; A61B 5/024; A61B 5/0408; A61B 5/0006; A61B 5/04017; A61B 5/0245; A61B 5/029; A61B 5/02438; A61B 5/0402; A61N 1/37247
See application file for complete search history.

(56) References Cited

U.S. PATENT DOCUMENTS

| 6,743,225 B2 * | 6/2004 | Sanchez et al. ............... 606/34 |
| 2004/0158295 A1 * | 8/2004 | Dyjach et al. ................ 607/25 |
| 2005/0038482 A1 * | 2/2005 | Yonce et al. ................... 607/27 |
| 2006/0015148 A1 * | 1/2006 | McCabe et al. ................ 607/9 |
| 2006/0135876 A1 * | 6/2006 | Andresen ............ A61B 5/0245 600/513 |
| 2012/0232417 A1 * | 9/2012 | Zhang .......................... 600/518 |
| 2014/0107509 A1 * | 4/2014 | Banet et al. ................. 600/515 |
| 2014/0128713 A1 * | 5/2014 | Banet et al. ................. 600/391 |

* cited by examiner

*Primary Examiner* — Rex R Holmes
(74) *Attorney, Agent, or Firm* — Michael A. Whittaker (57) ABSTRACT

The invention provides a system for evaluating a patient featuring: 1) an ECG-measuring system connected to the patient and configured to sense ECG information from the patient; 2) a data-acquisition system interfaced to a vital sign-monitoring system configured to sense vital sign information from the patient during an electro-physiology (EP) procedure; and 3) an external software system interfaced to both systems. The external software system includes a first software interface that receives ECG information measured from the patient by the ECG-measuring system, and a second software interface that receives vital sign and EP-related information from the data-acquisition system measured from the patient during an EP procedure. A database stores physiological and EP-related information measured from the patient before, during, and after the EP procedure. And an algorithm interfaced with the database determines an efficacy of the EP procedure by collectively analyzing information measured during each of these phases.

6 Claims, 7 Drawing Sheets

INTERNET-BASED SYSTEM FOR CHARACTERIZING PATIENTS UNDERGOING AN ELECTROPHYSIOLOGY PROCEDURE

FIELD OF THE INVENTION

The present invention relates to systems for facilitating cardiovascular procedures, e.g. electrophysiology (EP) procedures.

DESCRIPTION OF THE RELATED ART

Modern systems for electrocardiography (ECG) measure time-dependant waveforms, heart rate (HR), and information related to arrhythmia and other cardiac properties from ambulatory patients. These systems can characterize patients over short (e.g. 24-48 hours) periods using 'holter' monitors, or over longer (e.g. 1-3 weeks) using cardiac event monitors. Conventional holter or event monitors typically include a collection of ECG electrodes (typically 3 or 5), an ECG circuit that collects analog signals from the ECG electrodes and converts these into multi-lead ECG waveforms, and a computer processing unit that analyzes the ECG waveforms to determine cardiac information. Some modern ECG-monitoring systems include wireless capabilites that transmit ECG waveforms and numerical data through a cellular interface to an Internet-based system, where they are further analyzed to generate, for example, reports describing the patient. In less sophisticated systems, the ECG-monitoring system is worn by the patient, and then returned to a company that downloads all relevant information into a computer, which then analyzes it to generate the report. The report, for example, may be imported into the patient's electronic medical record (EMR). In most cases, the EMR avails the report to cardiologists or other clinicians, who then use it to help characterize the patient.

Nearly all conventional vital sign monitors include ECG monitoring systems characterize a patient's cardiac response. Such monitors typically measure multi-lead ECG waveforms that are processed by embedded software within the monitor to generate ECG waveforms and determine HR and a wide range of other cardiac properties.

During a conventional EP procedure, software systems can collect physiological information from the patient (e.g. vital signs and ECG waveforms), and then store this in the patient's EMR for future analysis by the cardiologist. Typically these systems interface with ECG-monitoring systems measure 12 leads of ECG waveforms, which a cardiologist then interprets to elucidate, diagnose, and ultimately treat the electrical activities of the patient's heart. During cardiac EP, an invasive catheter records spontaneous activity of the heart, as well as of cardiac responses to programmed electrical stimulation (PES). Cardiac EP procedures are performed to assess complex arrhythmia, elucidate symptoms, evaluate abnormal ECG waveforms, assess risk of developing arrhythmias in the future, and design and perform treatment. They typically feature therapeutic methods, such as radio frequency ablation of pre-determined portions of the heart corresponding to the patient's cardiac condition, in addition to the above-described diagnostic and prognostic procedures. ECG-monitoring devices used in the EP procedure measure the response of the injured or cardiomyopathic myocardium to PES on specific pharmacological regimens in order to assess the likelihood that the regimen will successfully prevent potentially fatal sustained ventricular tachycardia (VT) or ventricular fibrillation (VF) in the future. Sometimes a series of drug trials are conducted before and/or after an EP procedure to enable the cardiologist to select the one regimen for long-term treatment that best prevents or slows the development of VT or VF following PES. Other therapeutic modalities employed in this field include anti-arrhythmic drug therapy and implantation of pacemakers and automatic implantable cardioverter-defibrillators (AICDs). Such studies may also be conducted in the presence of a newly implanted or replaced cardiac pacemaker or AICD.

Modern implanted pacemakers and AICDs also include electronic circuitry for recording and storing cardiac parameters, such as arrhythmia information, HR, HR, variability, and data describing the performance of the implanted device. Typically the implanted device stores this information within a computer memory that cart be read over a short-range wireless interface by a specialized device within a cardiologist's office. Both the specialized device and implanted device are typically designed and manufactured by the same company. The specialized device typically includes a computer, display, and a wand that is placed over the implanted device to read information over the short-range interface. Once read, the computer stores information generated by the implanted device, and at a later time can import this information into the patient's EMR, where it can be used to further diagnose the patient.

Many conventional EMRs are large software systems hosted on computer servers within a hospital or medical clinic. Some EMRs reside in 'the cloud', meaning they are hosted on remote computer servers (located, e.g., in a third-party data center), which then avails a graphical user interface (GUI) to hospital clinicians with a conventional web browser. In some instances, hospital administrators and clinicians use either the EMR or a secondary software system to perform ancillary functions related to the EP procedure, such as scheduling, billing, and patient follow-up.

As described above, an array of hardware and software systems can collect and store a patient's cardiovascular information before a cardiologist conducts an EP procedure, during the actual procedure, and alter the patient leaves the hospital or medical, clinic. In theory, data daring each of these phases flows into the patient's EMR. But, in reality, even state-of-the art EMRs are only able to collect and store limited amounts of data from these systems, especially when multiple, disparate systems are used to monitor the patient. And typically the data are not organized or formatted in a way that allows robust analysis of the cardiovascular performance of multiple patients by processing large data sets measured before, during, and after an EP procedure.

SUMMARY OF THE INVENTION

The present invention provides an improved system that operates in the cloud to seamlessly collect cardiovascular data from a patient during each of the above-mentioned scenarios. For example, during an EP procedure, the system collects information describing ECG waveforms and their various features, HR and other vital signs, HR variability, cardiac arrhythmias, patient demographics, and patient outcomes, and stores them on an Internet-accessible computer system that can deploy a collection of user-selected algorithms. Before and after the procedure, the system also integrates with body-worn or implanted devices to collect similar data while the patient is ambulatory. A database interfaced with the software system stores physiological and EP-related information measured from the patient before, during, and after the EP procedure. And a selection of algorithm-based tools or computer code (e.g. software) associated with these tools that are interfaced with the database can collectively analyze information measured during each of these phases from large sets of patients. The analysis, for example, can yield reports that characterize the efficacy of a given procedure, or help a clinician improve a cardiac BP procedure for a given patient.

The algorithm-based tools or software associated with these tools can analyze individual components of ECG waveforms from a given patient to estimate or predict the condition of the patient, or determine the efficacy of the EP procedure as applied to the patient. Alternatively, these tools can collectively analyze components of ECG waveforms corresponding to large groups of patients receiving a particular EP procedure to estimate the overall efficacy of the procedure. Components of the ECG waveforms analyze in this manner are described in more detail below, and include i) a QRS complex; ii) a P-wave; iii) a T-wave; iv) a U-wave; v) a PR interval; vi) a QRS interval; vii) a QT interval; viii) a PR segment; and ix) an ST segment. The temporal or amplitude-related features of these components may vary over time, and thus the algorithmic-based tools within the system, or software associated with the algorithm-based tools, can analyze the time-dependent evolution each of these components. In particular, algorithmic-based tools that perform numerical fitting, mathematical modeling, or pattern recognition may be deployed to determine the components and their temporal and amplitude characteristics for any given heartbeat recorded by the system. More specifically, ECG waveforms may be numerically 'fit' with complex mathematical functions, such as multi-order polynomial functions. These functions may then be analyzed to determine the specific components, or changes in these components, within the ECG waveform. In related embodiments, ECG waveforms may be analyzed with more complex mathematical models that attempt to associate features of the waveforms with specific bioelectric events associated with the patient.

Each of the above-mentioned components corresponds to a different feature of the patient's cardiac system, and thus analysis of them according to the invention may determine or predict different cardiac conditions. These conditions and their associated component include: blockage of arteries feeding the heart (PR interval); aberrant ventricular activity or cardiac rhythms with a ventricular focus (QRS interval); prolonged time to cardiac repolarization and the onset of ventricular dysrhythmias (QT interval); P-mitrale and P-pulmonale (P-wave); hyperkalemia, myocardial injury, myocardial ischemia, myocardial infarction, pericarditis, ventricular enlargement, bundle branch block, and subarachnoid hemorrhage (T-wave); and bradycardia, hypokalemia, cardiomyopathy, and enlargement of the left ventricle (U-wave). These are only a small subset of the cardiac conditions that may be determined or estimated through analysis of the ECG waveform according to the invention.

Algorithmic-base tools, or software associated with these tools, can also analyze relatively long traces of ECG waveforms (spanning over seconds or minutes) measure before, during, and after the EP procedure to characterize: i) a given patient; ii) the efficacy of the EP procedure applied to that patient; iii) a given patient's need for an EP procedure; or iv) the overall efficacy of the EP procedure as applied to a group of patients. For example, analysis of relatively long traces of ECG waveforms in this manner may indicate cardiac conditions such as cardiac bradyarrhythmias, blockage of an artery feeding the heart, acute coronary syndrome, advanced age (fibrosis), inflammation (caused by, e.g., Lyme disease or Chaga's disease), congenital heart disease, ischaemia, genetic cardiac disorders, supraventricular tachycardia such as sinus tachycardia, atrial tachycardia, atrial flutter, atrial fibrillation, junctional tachycardia, AV nodal reentry tachycardia and AV reentrant tachycardia, reentrant tachycardia, Wolff-Parkinson-White (WPW) Syndrome, Lown-Ganong-Levine (LGL) Syndrome, and ventricular tachycardia. Likewise, analysis of these cardiac conditions by analyzing the ECG waveforms may indicate the efficacy of the EP procedure.

In one aspect, the invention features a system for evaluating a patient that includes: i) a first ECG-measuring system that senses ECG information from the patient; ii) a data-acquisition system interfaced to a vital sign-monitoring system that senses vital sign information from the patient during a cardiac EP procedure; and iii) a software system interfaced to both the ECG-measuring system and the data-acquisition system. The software system typically connects to the Internet, meaning that it operates in the cloud and can be hosted on a remote server that can reside outside of the hospital. It can include a GUI (e.g. a web page), rendered by a web browser, which a user may view with a computer or mobile device, such as a cellular telephone or tablet computer. The software system features: i) a first software interface that receives ECG information sensed by the ECG-measuring system; ii) a second software interface that receives vital sign information from the data-acquisition system and sensed by the vital-sign monitoring system; a iii) a database that stores ECG information sensed from the patient before and after the EP procedure, and vital sign information sensed during the EP procedure by the vital sign monitor; and iv) an algorithm that evaluates the EP procedure by collectively analyzing ECG information sensed from the patient before, during and/or after the EP procedure.

In other embodiments, the algorithm compares a first set of parameters extracted from ECG information sensed from the patient before the EP procedure to a second set of parameters extracted from ECG information sensed from the patient after the EP procedure. The first and second sets of data are collected from either an individual patients or large groups of patients. Using this information, the algorithm can estimate the efficacy of a given EP procedure, and convey this in the form of an Internet-accessible report to a clinician. For example, operating in this capacity, the algorithm can analyze HR information, arrhythmia information, or morphology of the ECG waveform, e.g. an ECG QRS complex or QT interval. It then uses this information to evaluate a specific procedure.

In other embodiments, the database is configured to store information from a collection of patients. Here, the system may deploy algorithms that rely on advanced computational techniques, such as a numerical fitting algorithm, mathematical modeling, and/or pattern recognition. The algorithm may calculate, for example, statistics describing the efficacy of an EP procedure performed on each patient within the group of patients, and following the calculation generate a report describing the statistics. In general, the system can perform a wide range of algorithms and, in response generate multiple types of clinical reports to improve the efficacy of the EP procedure.

In other embodiments, the ECG-measuring system is a body-worn system that can include, e.g., an analog ECG front end, a processing system, and an interface to the Internet. The interface can be either wired or wireless, and may include a conventional mobile device, such as a cellular telephone or tablet computer. The mobile device used to transmit information to the system may be the same one used to view reports and GUIs generated by the system. The system can include both first and second ECG-measuring systems than can be the same system, or different systems. Typically the first ECG-measuring system senses ECG information from the patient before the EP procedure, and the second ECG-measuring system senses ECG information from the patient after the EP procedure. Both the first and second ECG-measuring systems can be body-worn systems that are worn on the outside of the patient's body. Alternatively, one or both of the ECG-measuring systems can be an implanted system, e.g. one that comprises a pacemaker or other AICD.

The invention has many advantages. In general, a cloud-based system that connects to the Internet from a remote server typically offers more flexibility than a system that is deployed in the same facility (e.g. a hospital or medical clinic) used to perform the EP procedure. With such a system, information from multiple, diverse patient groups can be collectively analyzed to perform sophisticated research relating to EP and other cardiovascular procedures. The same system that performs the research can also generate reports and other materials using data from large groups of patients that can easily be dispersed to clinicians, thereby given them the tools to improve their clinical practice. Moreover, cloud-based systems are inherently easier to maintain (e.g. deploy, update) compared to hosted systems deployed at a collection of facilities, as new software builds and enhancements can be made on a single server, and then instantaneously deployed to multiple Internet-connected sites.

These and other advantages will be apparent from the following detailed description, and from the claims.

DETAILED DESCRIPTION OF THE INVENTION

Then invention provides a cloud-based system that seamlessly collects cardiovascular and other patient-related data before, during, and after an EP procedure, stores data from large groups of patients in a relational database, and then analyzes these data to evaluate the efficacy of the procedure. The system may also integrate with secondary software systems that facilitate management and billing of EP procedures. The database integrates with algorithms that process the data and further distil it to provide useful information to a clinician. For example, in some embodiments, the system collects information describing ECG waveforms and various components found therein, HR, HR variability, cardiac arrhythmias, performance of the implanted device, patient demographies, and patient outcomes, and stores them on an Internet-accessible computer system that can deploy a collection of algorithms. Using a simple graphical interface available through the Internet, clinicians can deploy the algorithms to improve their practice and better manage their patients.

Figure 1:
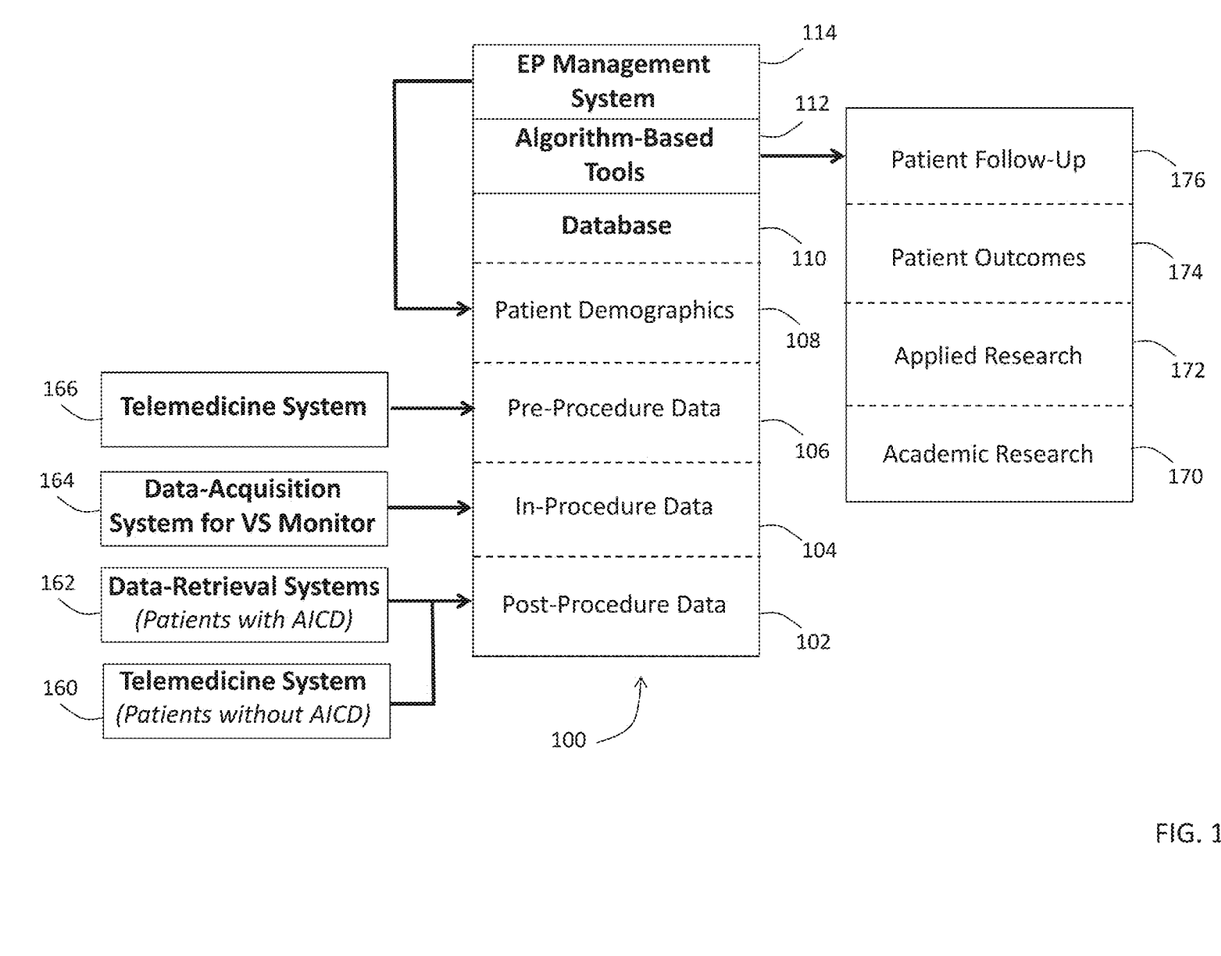
FIG. 1 shows a schematic drawing of a system according to the invention that collects cardiovascular information from a patient and a collection of hardware devices, stores the information in a database, and collectively analyses the information to diagnose the patient.

FIG. 1 shows a system 100 according to the invention. The system 100 is a software system that features a collection of computer code, and typically operates on a remote computer system (e.g. one residing in a data center) connected to the Internet. The system 100 features a database 110, a set of algorithm-based tools 112, and an EP management system 114. A GUI may render each of these components. The database 110 includes an array of data fields that store patient demographics 108, pre-procedure data 106, in-procedure data 104, and post-procedure data 102. These data are typically collected by multiple physiological monitoring systems. For example, a patient can wear a telemedicine system 166, such as a body-worn ECG monitoring system, to collect the pre-procedure data 106 outside of the hospital. Such a system, which is described in more detail with reference to FIG. 6, typically collects real-time ECG waveforms, arrhythmia data, HR data, and other information from the patient during a short period (e.g. a few days to several weeks) before the actual EP procedure. These data can be ported into the pre-procedure data field 106 through a wired or, more preferably, a wireless interface, such as a cellular interface. In embodiments, the software system 100 and telemedicine system 166 are designed to integrate with one another. In this case, the telemedicine system may be programmed to automatically send information to the system 100, i.e. it is programmed to automatically send information to a specific IP address associated with the system. Alternatively, a third-party vendor may manufacture the telemedicine system 166, and this in turn integrates with the system 100 through a software interface, such as a web service interface. In other embodiments, the system 100 collects pre-procedure physiological data from a collection of telemedicine systems 166, each manufactured by one or more outside vendors. In each case, a schema associated with the pre-procedure data fields 106 is used to describe the specific data elements that flow into the database 110.

The system 100 collects data during the actual EP procedure with a data-acquisition system 164 that integrates with a vital sign (VS) monitor. The data-acquisition system 164, for example, can include both hardware and software components, e.g. a serial or parallel data cable and a software system that receives data from the VS monitor, and then parses it appropriately. Alternatively, the data-acquisition system 164 can be a software interface to an EMR system. In both cases, the data-acquisition system 164 extracts time-dependent waveforms and numerical vital signs such as HR, blood pressure, respiratory rate, blood oxygen, and temperature from the VS monitor used during the EP procedure. In a preferred embodiment, the data-acquisition system 164 extracts data in a quasi-continuous manner daring the EP procedure, e.g. a new, updated numerical value is extracted every second or so. Once extracted, these data are stored in the in-procedure data fields 104 associated with the database 110, and then used for follow-on analysis as described in more detail below.

After the EP procedure is complete, data can be collected from the patient with a data-retrieval system 162 that extracts data from an internal memory associated with an implanted device (e.g. a pacemaker or other AICD), or a telemedicine system 160 that measures data from a patient with or without an implanted device. These data are stored in the post-procedure data fields 102. The data-retrieval system 162 is typically a computer-based system that resides in a cardiologist's office and includes a short-range wireless component that, when waved over a patient's pacemaker, receives data and then stones in memory associated with the computer-based system. For example, the short-range wireless component may rely on inductive magnetic coupling to remove physiological data associated with the patient, along with data associated with the performance of the implanted device, e.g. the number and time/date of defibrillation shocks, battery information. Once data are stored on the computer-based system, the data-retrieval system 162 transfers it over to the post-procedure data field 102 for future analysis. In embodiments, for example, the data-retrieval system 162 may include manufacturer-specific software, such as Medtronic's Paceart® System, to facilitate data extraction and transfer. The Medtronic Paceart® System organizes and archives data for cardiac devices across manufacturers and serves as a central repository for a patient's arrhythmia and other information. The system serves as a gateway through which data flows from the computer-based system into a clinic's electronic health record EMR.

A telemedicine system 160 supplies data for the post-procedure data field 102 for patients that lack an AICD. Such a telemedicine system 160 is comparable or, more preferably, identical to the telemedicine system 166 used to supply data for the pre-procedure data field 106. It is typically a body-worn system, used to characterize a remote, ambulatory patient, that includes an ECG-monitoring system and computing module that measures, digitizes, and processes analog ECG waveforms to determine parameters such as HR, arrhythmia information, and motion-related information from the patient. The telemedicine system 166 may include a wireless system that sends data from the ambulatory patient to the post-procedure data field 102. Typically the telemedicine system 160 is worn for a period ranging from 1-2 days to several weeks. In other embodiments, the patient uses the telemedicine system 160 on a semi-permanent basis to collect data for a short period time each day. For example, the telemedicine system 160 may be used by the patient's bedside to collect data each night when the patient is sleeping.

A collection of algorithm-based tools 112 interface with the database 110 within the system 100 to process data stored in the pre-procedure 106, in-procedure 104, and post-procedure 102 data fields to generate usable information for the clinician. In preferred embodiments, the algorithm-based tools 112 are embedded within the EP management system 114, thereby providing clinicians with a single, integrated system that allows them to schedule procedures, perform billing operations, manage existing patients, and research new treatment strategies that may be effective with new patients. For example, the algorithm-based tools 112 may include modules that facilitate patient follow-up 176, help determine patient outcomes 174, and perform applied 172 and academic 170 research studies on large groups of patients to help determine, e.g., the efficacy of certain treatment methodologies. In embodiments, result from the applied 172 and academic 170 research studies could be made available to clinicians through reports generated by the system 100.

Figure 2:
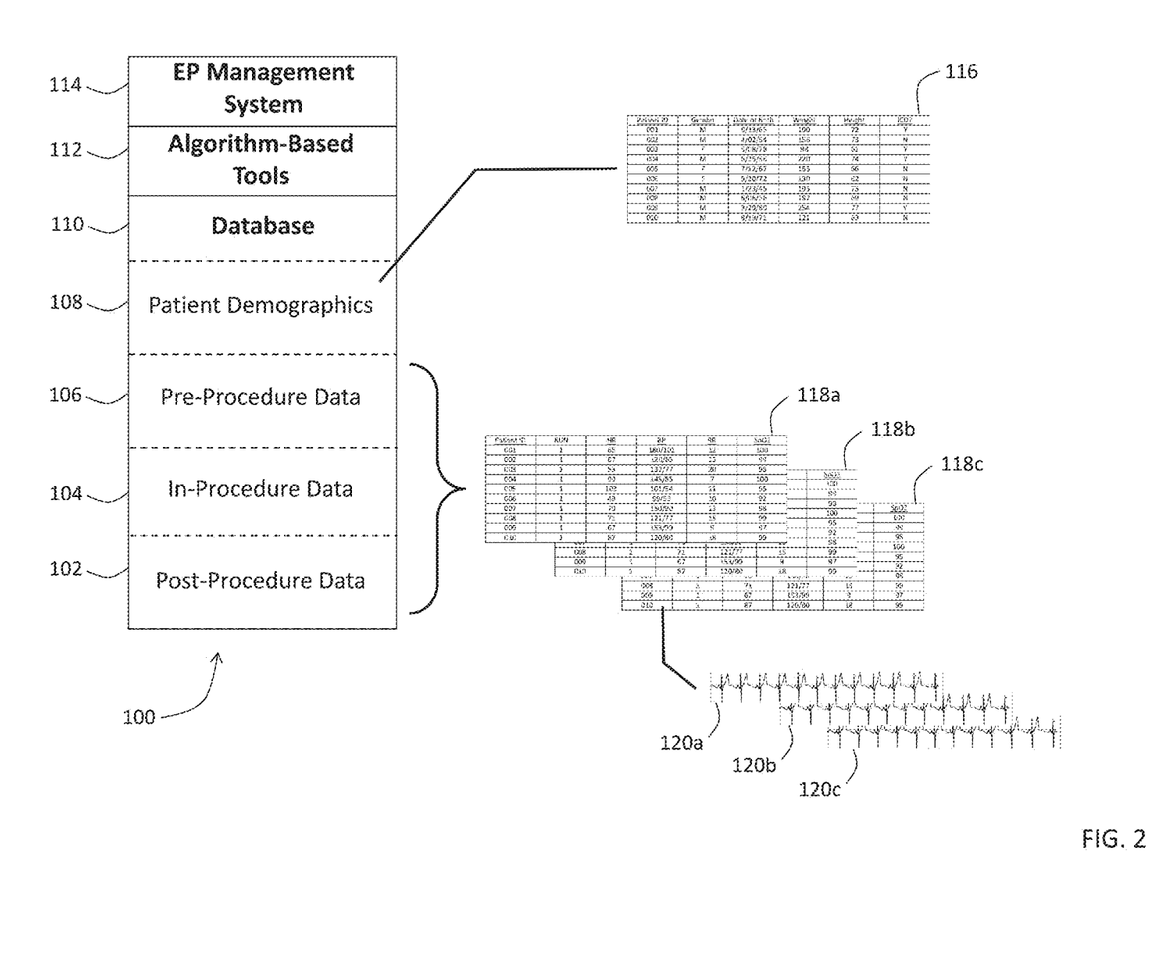
FIG. 2 shows a schematic drawing of the system of FIG. 1, featuring database tables that describe patient demographies, physiological information, and ECG waveforms collected from a patient.

FIG. 2 shows examples of simple data fields within the database 110. In embodiments, for example, the database 110 includes a 'Patient Demographics' data field 108 that features simple parameters such as a patient identifier (e.g. number), their gender, date of birth, along with simple biometric parameters such as weight, height, and whether or not the patient has an AICD. For example, these data can be organized in standard tables used by commercially available relational databases, such as Microsoft SQL Server, MySQL, IBM DB2, and Oracle. Typically the patient identifier within the Patient Demographics field 108 is a database 'key' that links a particular patient to other data fields. For example, other data fields within the database 110, such as the Pre-Procedure 106. In-Procedure 104, and Post-Procedure 102 data fields, use this key to link physiological data measured during these particular periods to the patient. These data are found in new tables 118a-c in the database, and typically include physiological data (e.g. numerical values and waveforms) describing parameters such as HR, systolic and diastolic blood pressure (BP), respiratory rare (RR), and blood oxygen (SpO2). Typically these parameters are measured over time (e.g. in a continuous or quasi-continuous manner), and then identified in the tables 118a-c by a 'Run' number that sequentially increases over time. As described above, data for the tables 118a-c is typically measured with a hardware component attached to the patient, such as a telemetry monitor that an ambulatory patient wears outside of the hospital, an AICD, or by a VS monitor used to measure the patient during an actual EP procedure.

The database may also associate numerical physiological data for each run with a physiological waveform 120a-c that is analysed to extract the particular datum. For example, as shown in FIG. 2, the above-mentioned hardware component may measure time-dependent ECG waveforms 120a-c that yield information such as HR and arrhythmia information, and are thus stored in the database. Such waveforms may be processed with the algorithm-based tools described with reference to FIG. 1, such as numerical 'fitting' or beat picking algorithms, to better diagnose a patient's condition. Although FIG. 2 only shows single-lead ECG waveforms, other physiological waveforms can also be measured, stored, and then processed with the algorithm-based tools described above. These waveforms include multi-lead ECG waveforms, photoplethysmogram (PPG) waveforms that yield SpO2, arterial waveforms that yield BP, and impedance cardiography (ICG) waveforms that yield RR and cardiac parameters such as stroke volume and cardiac output. In embodiments, these waveforms may be associated with another table that includes annotation markers that indicate fiducial points (e.g., the QRS complex in an ECG waveform) associated with certain features in the waveforms. The algorithm-based tools may also process these annotation markers to perform simple patient follow-up, estimate patient outcomes, and do applied and academic research, as described above.

In related embodiments, ECG waveforms may be analyzed with more complex mathematical models that attempt to associate features of the waveforms with specific bioelectric events associated with the patient. For example, mathematical models can be deployed that estimate ECG waveforms by interactively changing the estimated timing associated with depolarization and repolarization of a simulated ventricular surface, as well as the strength of the depolarization and repolarization. The timings and signal strengths associated with these models can then be collectively analyzed to simulate an ECG waveform. The simulated ECG waveform can then be compared to the waveform actually measured from the patient to help characterize their cardiac condition, or the efficacy of the EP procedure that addresses this condition. In general, a wide range of physiological and device-related parameters can be stored in the data tables described above. Examples of some of these data fields corresponding to specific ECP procedures are shown below in Table 1.

In embodiments, commercially available software tools, such as Mortara's E-Scribe Rx and VERITASÔ ECG algorithms, may be interlaced with the database 110 and used to analyze ECG waveforms measured from the patient. These software tools are designed to analyze complex, multi-lead ECG waveforms to determine complex arrhythmias, VF, VT, etc.

Figure 3:
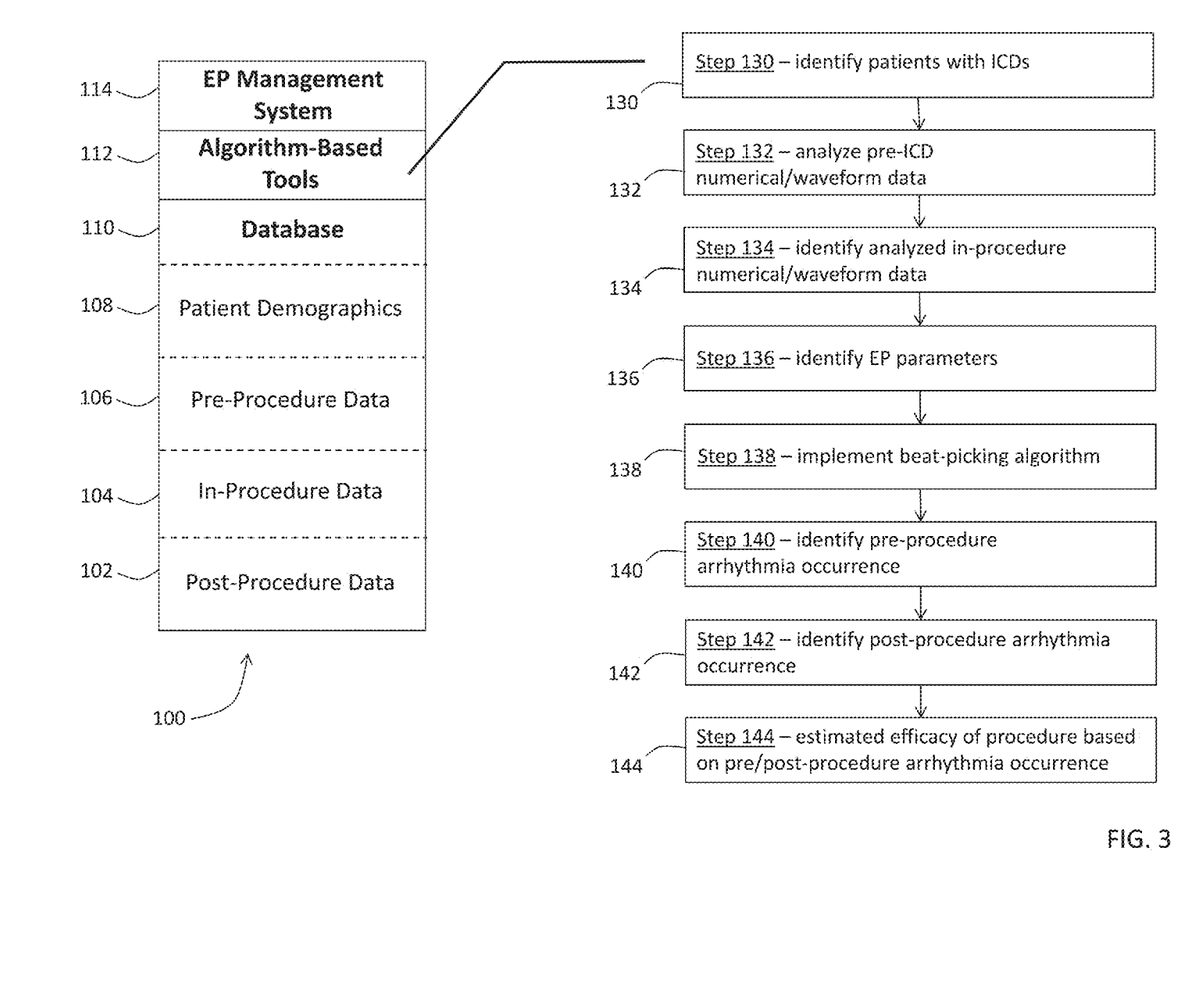
FIG. 3 shows a schematic drawing of the system of claim 1, featuring an algorithm integrated with the database tables of FIG. 2 that analyses a patient's cardiovascular information.

FIG. 3 shows a simple example of an algorithm-based tool 112 that analyzes patient data within the database to estimate a patient's outcome. In this particular algorithm-based tool 112, computer code associated with the database analyzes data fields to first identify patients with AICDs (step 130). The code then collects pre-ICD (step 132) and in-procedure (step 134) numerical/waveforms data, along with parameters from the patient's EP procedure (step 136), and readies them for analysis. Parameters collected during the patient's EP procedure include parameters associated with the EP catheter used during the EP procedure (such as those described in Table 1), potentials applied by the catheter and their timing, two and three-dimensional images (measured, using either Doppler/echo or MRI). The algorithm-based tool 112 then collectively analyzes these data, and implements a beat-picking algorithm (step 138) to further characterize ECG waveforms measured during steps 134 and 136. The beat-picking algorithm can determine parameters such as induced arrhythmia, effective refractory periods, characteristics of specific components within the patient's ECG waveform, e.g. the QRS complex, width of the P-wave, QT period and dispersion, and instantaneous HR.

TABLE 1 data fields associated with specific EP procedures

| Description of Data Field | # of Possible Values | Example Values |
|---|---|---|
| Ablated Locations | 35 | AV Node Modification (Fast pathway), Bundle Branch, Complex fracionated atrial electrograms (CFAE), Crista Terminalis, LA Anteroseptal line, LA CS Line, Left atrium, RIGHT ATRIUM, Accessory Pathway, AV Node, Cavo-tricuspid isthmus, Endocardial, Epicardial, Fast pathway, Intermediate pathway, LEFT CIRCUMFERENTIAL PULMONARY, Segmental antral left lower pulmonary vein, Segmental antral left lower pulmonary vein, MITRAL ISTHMUS, Fast pathway, Left Atrial Linear (Mitral Isthmus), Right Circumferential Pulmonary, Left Atrial Linear (Mitral Isthmus), Endocardial, Right Circumferential Pulmonary, EPICARDIAL, Segmental antral right lower pulmonary vein, Left Atrial Linear (Roof), Segmental antral right upper pulmonary vein, Segmental antral right upper pulmonary vein, SVC, Slow pathway, Segmental antral right lower pulmonary vein. |
| Sub-Locations | 106 | Left Circle, LV Septal Basal, CS middle, Lower crista, LA septal wall, Mitral Valve Annulus, RA lateral wall, Left Antero-Lateral, Non Coronary Cusp, Upper crista, RVOT Anterior, LA Scar, Atrio-Ventricular, Left Lateral, Right Mahaim, CS proximal, Atrio-Fasicular, Right Mid-Septal, RV Posterior Basal, CS distal, LA appendage, LA anterior wall, Lower Loop, Left Aortic Cusp, LV anterior Fascicle, LA septum, RV Anterior Apical, LV Posterior Mid, LV Posterior Fascicle, LV Posterior Apical, RV Anterior Mid, LLPV, RLPV, RVOT Free Wall, RV Septal Apical, RV Lateral Mid, Mitral Isthmus (with CS), Right Postero-Lateral, RBB, LV Lateral Basal, Left Antero-Septal, RA septal wall, LV Septal Apical, MVA anterior, LV Outlow Tract, Upper Loop, Pulmonary Artery, Right Antero-Lateral, TVA lateral, Right Aortic Cusp, RA Scar, Right Posterior, RA anterior wall, Mitral Isthmus (endocardial only), RV Posterior Apical, CSos, LV Anterior Mid, RV Lateral Basal, Left Mahaim, TVA posterior, RA poseterior wall, Nodo-Fasicular, LV Lateral Mid, RA appendage, Cavo-Tricuspid Isthmus, LA lateral wall, RVOT Posterior, Middle crista, Superior Vena Cava, Left Posterior, LV Anterior Basal, Fossa ovalis, LV Septal Mid, LUPV, Diverticular, Diverticuar, SVC, Non-Coronary Aortic Cusp, TVA anterior, Right Lateral, RVOT Septal, MVA septal, RUPV, LA posterior wall, Right Postero-Septal, MVA posterior, Nodo-Ventricular, MVA lateral, RV Anterior Basal, LV |

TABLE 1-continued data fields associated with specific EP procedures

| Description of Data Field | # of Possible Values | Example Values |
|---|---|---|
| | | Lateral Apical, Left Postero-Septal, Right Antero-Septal, LVOT, RV Septal Mid, Left Postero-Lateral, RV Septal Basal, LA roof, Left bundle branch, LA poseterior wall, RV Posterior Mid, RA septum, RV Outflow Tract Anterior, RV Lateral Apical, Csos, LV Posterior Basal, Right Circle |
| Access Locations | 29 | Left Subclavian Vein, Right Antecubital Vein, Right Femoral Vein, Right Subclavian Vein, Right Lower Extremeties/Thigh, Left Antecubital Vein, Superficial Right Leg, Superficial Right Hand/Forearm Vein, Deep Right Hand/Forearm Vein, Right Femoral Artery, Superficial Right Arm Vein, Superficial Left Hand/Forearm Vein, Deep Right Arm Vein, Deep Right Arm Vein, Deep Left Hand/Forearm Vein, Left Femoral Vein, Left Lower Extremeties/Thigh, Right Foot, Right Internal Jugular Vein, Superficial Left Leg, Deep Right Leg, Left Femoral Artery, Left Internal Jugular Vein, Deep Left Arm Vein, Left Radial Artery, Right Radial Rrtery, Superficial Left Arm Vein, Left Foot, Deep Left Leg |
| Arrhythmia Mechanism | 20 | Idiopathic ventricular tachycardia, Atrial Fibrillation Paroxysmal, AV Nodal Reentry (fast-slow), AV Nodal Reentry (slow-slow), Premature ventricular contractions, Atrial Fibrillation Persistent Atypical Left Atrial Flutter, Atypical Mitral Isthmus Flutter, Bundle Branch Reentry VT, Inappropriate Sinus Tachycardia, Structural ventricular tachycardia - Dilated Cardi, AV Nodal Reentry (slow-fast), Focal Atrial Tachycardia, Antidromic AV reentrant tachycardia, Reverse Typical Atrial Flutter, Atypical Right Atrial Flutter, Typical Atrial Flutter, Structural ventricular tachycardia - Ischemic Card, Wolff-Parkinson-White syndrome, Orthodromic AV reentrant tachycardia |
| Arrhythmia Mechanism Types | 10 | Typical Atrial Flutter, AV nodal reentry (slow-slow), AV nodal reentry (slow-fast), Antidromic AV reentrant tachycardia (ART), Reverse Typical Atrial Flutter, Ventricular tachycardia, Orthodromic AV reentrant tachycardia (ORT), Atrial Fibrillation, Atypical Atrial Flutter, AV nodal reentry (fast-slow) |
| Arrhythmia Observations | 9 | Vagal Effect, Arrhythmogenic Veins RUPV, Arrhythmogenic Veins LLPV, Concealed Accessory Pathway, Negative CSM, WPW, Positive CSM, Arrhythmogenic Veins LUPV, Arrhythmogenic Veins RLPV |
| Axis Deviations | 6 | Left, Left Inferior, None, Right Inferior, Right, Left Superior |
| Mapping Systems | 8 | Carto 3D electro-anatomical, Fluoroscopy, Ensite 3D Balloon Array, ESI NavX 3D electro-anatomical |
| Energy Sources | 6 | Cryoablation, Laser, Ultrasound, Other, Radiofrequency |
| Morphology | 8 | |
| Pacing Site | 13 | LVA, LRA, LA, RVOT, RVA, LVB, CSP, CSP, LLA, HRA, CSD, CSM, LVOT |
| lu_abl_result | 51 | Intermediate pathway block - not reinducible, Partially Isolated, ORT Reinducible, Right bundle branch block, AV Node Block, AV Node Modified, Fast pathway block - not reinducible, VT Not-reinducible, Conduction Block, Isolated, AVNRT Reinducible, Mitral Isthmus Block (bidirectional), ORT Not Reinducible, Bidirectional CTI Block, AFL Terminated, PVCs eliminated, LLPV Isolated, Left bundle branch block, VT Slowed, WPW Terminated, FAT terminated, ORT Terminated, Reduction in electrogram amplitude to less than 0.5 mV, RMPV Isolated, AP block, not reinducible, RUPV Isolated, AF Terminated, Complete AV Block, Slow pathway block - not reinducible, AF Converted to AFL, AFL Not Reinducible, AP Block, Reduction in electrogram amplitude to less than 0., VT Terminated, Mitral Isthmus Conduction Delay Only, LUPV Isolated, Single AV nodal echo only, ART Reinducible, AF Termination, AP Block, Not Reinducible, ART Not Reinducible, ART Terminated, WPW Reinducible, Mitral Isthmus Block (unidirectional), CTI conduction |

TABLE 1-continued data fields associated with specific EP procedures

| Description of Data Field | # of Possible Values | Example Values |
|---|---|---|
| | | delay, Incomplete AV Block, Mitral Isthmus Conduction Delay, AP block (antegrade and retrograde), RLPV Isolated, AP block (antegrade only), Unidirectional CTI Block |
| Structural Observations | 8 | Atrial Septal Defect, Patent Foramen Ovale, Common OS Left, Atrial Scarring, LA Thrombus, Common OS Right, Pericardial Effusion |
| Termination Methods | 11 | Cardioversion, Ablation, Burst, Verapamil, Adenosine, Spontaneous, Metropolol, Pvc, Procainamide, Ibutilide, Pac |
| Access Type | 21 | Direct Cutdown, Percutaneous, Epicardial, Swan-Ganz Line, Tunneled Central Line, Arterial Line, Central Venous Pressure Line, Sheath - Hansen, Sheath - Transseptal, Peripherally Inserted Central Catheter, Pulmonary Artery Catheter, Shunt, Sheath - Steerable, Sheath - Standard short, Sheath - Preformed long, Central Venous Line, Peripheral IV, Implantable Port |

Using these technologies, the algorithm-based tool 112 can perform simple functions like identifying pre-procedure (step 140) and post-procedure (step 142) arrhythmia occurrences, and then comparing these to determine the efficacy of the procedure (step 144). Many other algorithm-based tools, of course, are possible within the scope of this invention.

Figure 4:
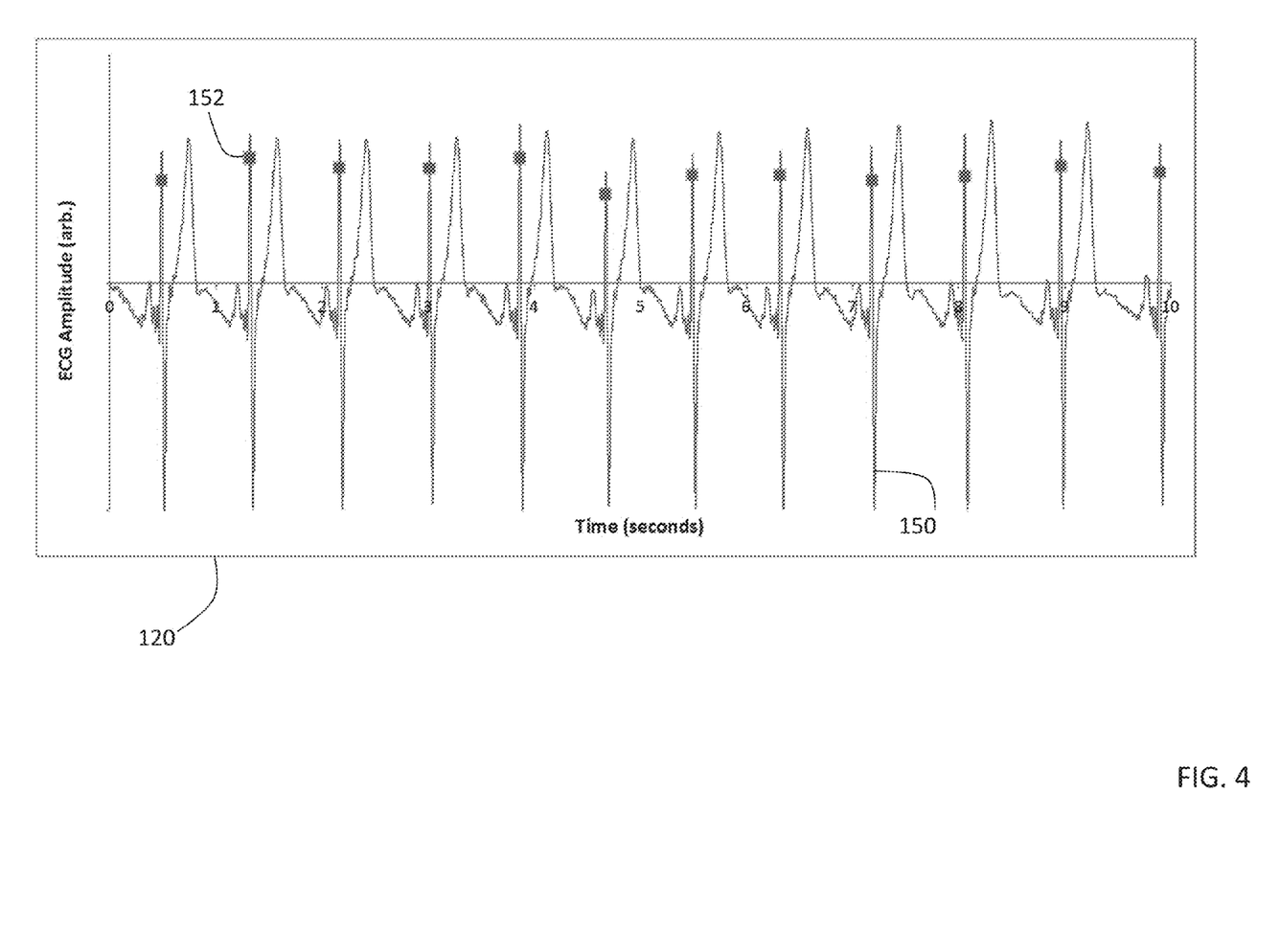
FIG. 4 shows a time-dependent ECG waveform that can be stored in the database of FIG. 1 and then analyzed with a beat-picking algorithm.

FIG. 4 shows an example of an ECG waveform 150 that is measured from a patient (e.g., before the EP procedure), stored in the database, and then analyzed by an algorithmic-based tool such as that described with reference to FIG. 3 to estimate the patient's cardiac performance. The ECG waveform, which in this case corresponds to a relatively healthy patient, 150 features a collection of equally spaced, time-dependent data points that are defined by a sampling rate of an ECG monitor (such as that shown in FIG. 6), which in this case in 500 Hz. The waveform features a sharply varying peak, called the QRS complex, which indicates initial depolarization of the heart and informally marks the onset of the patient's cardiac cycle. Each heartbeat yields a new QRS complex. After a few hundred milliseconds, a relatively slowly varying feature called the T-wave follows the QRS complex. In general, each patient features a unique ECG waveform from which the algorithmic-based tools can extract important cardiac information. In FIG. 4, a simple algorithmic-based tool called a 'beatpicker' analyzes the ECG waveform 150 to determine the patient's HR and arrhythmia information. In this application, the beatpicker uses an algorithm (called the Pan-Thompkins algorithm) that determines the temporal location of the QRS complex corresponding to each heartbeat. The Pan-Thompkins algorithm typically includes the following steps: i) filtering the ECG waveform to remove any high-frequency noise; ii) taking a mathematical derivative of the waveform; iii) squaring the waveform; iv) signal averaging the waveform; and v) finding the peaks of the waveform processed with steps i)-iv). Locations of the QRS complex form waveforms processed in this manner are shown in the figure by a collection of gray squares 152. Once the collection of QRS complexes is located, the algorithmic-based tool can determine the patient's HR and arrhythmia information using well-known techniques in the art.

The ECG waveform 150 described above is relatively simple, and other than a relatively tall T-wave, lacks any complicated features that challenge conventional beatpickers. However, such features are not uncommon amongst cardiac patients, and thus the beatpicker must be sophisticated enough to analyze them. Moreover, the ECG waveform 152 shown in FIG. 4 only corresponds to a single lead, and thus is relatively unsophisticated and lacks information describing complex cardiovascular performance. Typically, the system according to this invention analyzes multi-lead ECG waveforms 180, such as those shown in FIG. 5. Multi-lead ECG waveforms can contain information from 5, 7, and even 12-lead ECGs. In general, these types of ECG waveforms are required to evaluate the complex cardiovascular performance associated with patients that would most benefit from the present invention.

For example, in embodiments, algorithmic-based tools according to the invention, or software associated with these tools, can also analyzed relatively long traces of ECG waveforms (spanning over seconds or minutes) measured before, during, and after the EP procedure to characterize: i) a given patient; ii) the efficacy of the EP procedure applied to that patient; iii) a given patient's need for an EP procedure; or iv) the overall efficacy of the EP procedure as applied to a group of patients. Analysis of the relatively long traces of ECG waveforms in this manner may indicate cardiac conditions such as cardiac bradyarrhythmias, blockage of an artery feeding the heart, acute coronary syndrome, advanced age (fibrosis), inflammation (caused by, e.g. Lyme disease or Chaga's disease), congenital heart disease, ischaemia, genetic cardiac disorders, supraventricular tachycardia such as sums tachycardia, atrial tachycardia, atrial flutter, atrial fibrillation, junctional tachycardia, AV nodal reentry tachycardia and AV reentrant tachycardia, reentrant tachycardia, Wolff-Parkinson-White (WPW) Syndrome, Lown-Ganong-Levine (LGL) Syndrome, and ventricular tachycardia. Likewise, analysis of these cardiac conditions by analyzing the ECG waveforms may indicate the efficacy of the EP procedure.

Typically, before the algorithmic-based tool deploys the beatpicker, it is analyzed against well-known databases, such as the MIT arrhythmia database or the American Heart Association database, to determine its performance. Beatpickers with a performance of about 95% or greater, as evaluated relative to these standards, are typically categorized as acceptable. Alternatively, as described above, the algorithm-based tools may integrate with commercially available tools for analyzing ECG waveforms, such as those developed and marketed by Mortara.

Figure 5:
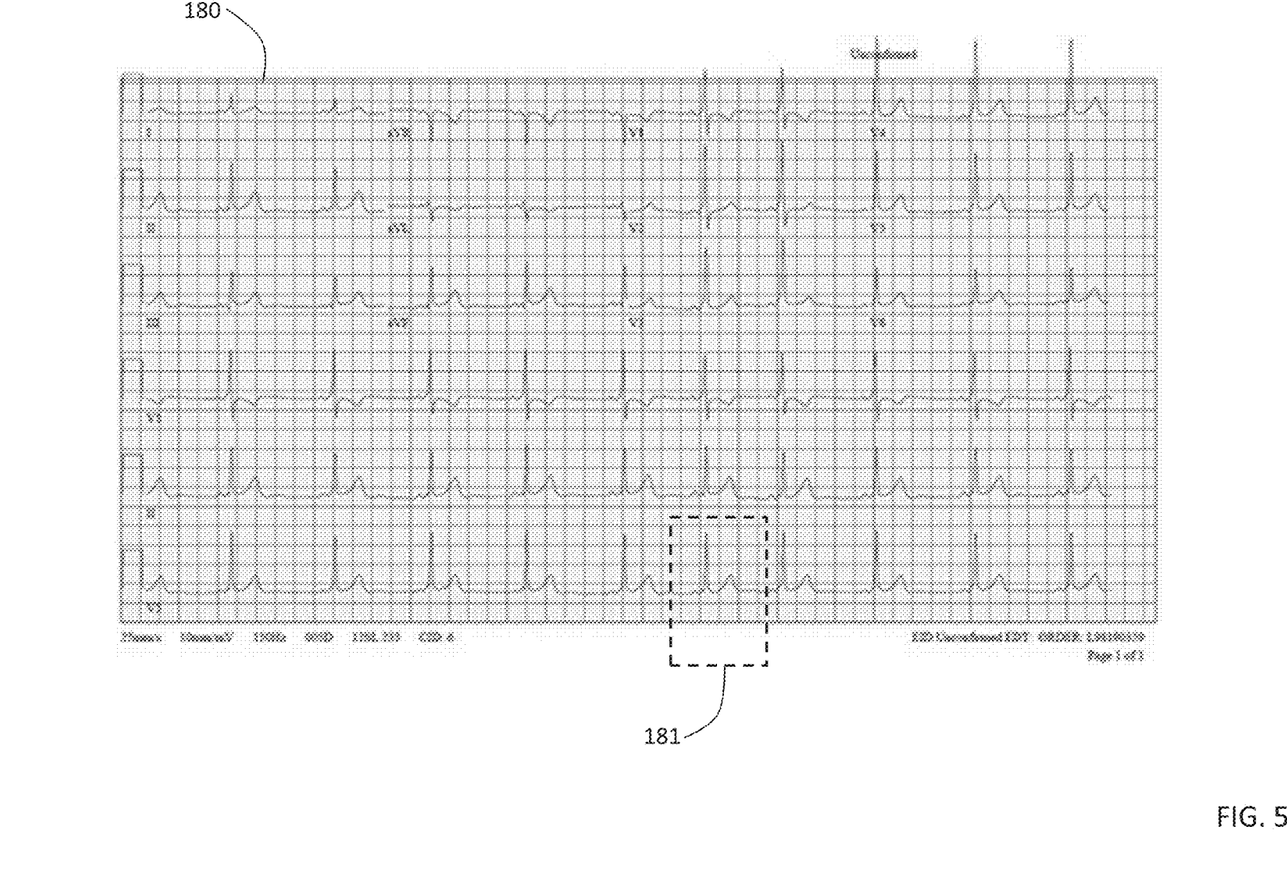
FIG. 5 shows a multi-lead ECG waveform stored in the database of FIG. 1.
Figure 6:
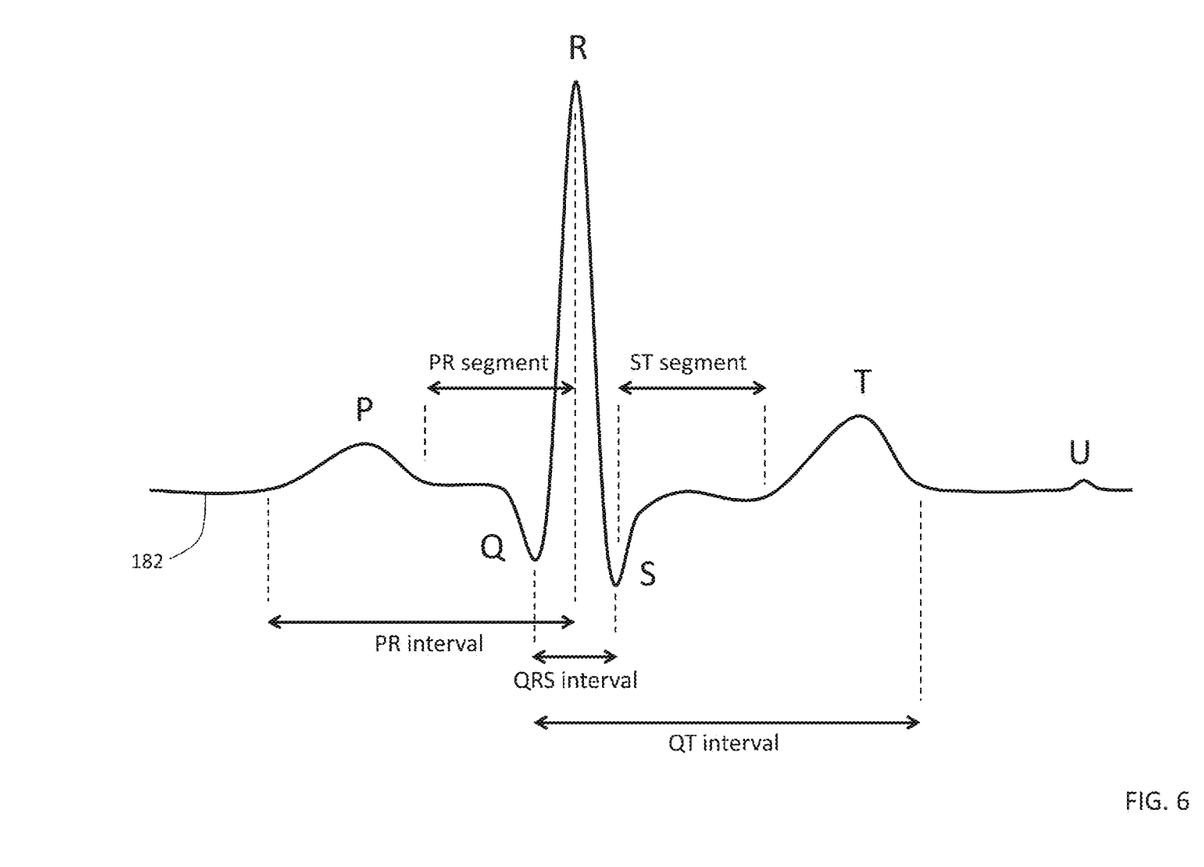
FIG. 6 shows a waveform 'snippet' taken from an ECG waveform in FIG. 5 that indicates various features associated with a patient's cardiac cycle.

FIG. 6 shows a waveform snippet 182 found within the ECG waveform that is shown in the dashed box 181 of FIG. 5. The waveform snippet 182 corresponds to a single heartbeat. Waveform snippets 182 may be collected before, during, and after an EP procedure, and are typically analyzed after they are stored in the database, as described above. Algorithm-based tools within the system, or software components within the algorithm-based tools, may analyze one or more waveform snippets 182 generated by a given patient to predict certain cardiac conditions assigned to that patient. Alternatively, the software may collectively analyze waveform snippets corresponding to large groups of patients to evaluate, e.g., the efficacy of a certain aspect of an EP procedure, or predict how a given EP procedure is likely to affect a given patient.

As shown in figure, the waveform snippet features the following components; i) a QRS complex; ii) a P-wave; iii) a T-wave; iv) a U-wave; v) a PR interval; vi) a QRS interval; vii) a QT interval; viii) a PR segment; and ix) and ST segment. Algorithmic-based tools within the system, or software associated with the algorithm-based tools, can analyze each of these components and their evolution over time as described above. In particular, algorithmic-based tools that perform numerical fitting or pattern recognition may be deployed to determine the components and their temporal and amplitude characteristics for any given heartbeat recorded by the system. Each component corresponds to a different feature of the patient's cardiac system. For example, the PR interval (which typically has a duration between about 120-200 ms) represents the time from firing of the patient's SA node to the end of the delay of their AV node. A prolonged PR interval, or a PR interval that is inconsistent over time, may indicate blockage of an artery feeding the patient's heart. Alternatively, a shortened or non-existent PR interval may indicate a cardiac condition such as tachycardic, junctional, ectopic, or ventricular rhythms. The QRS interval, which is typically between 40-100 ms, represents the travel time of electrical activity through the patient's ventricles and ventricular depolarization that drives contraction of the heart. QRS intervals that are longer than this, or that feature a 'notch', can indicate aberrant ventricular activity or cardiac rhythms with a ventricular focus.

Variation in the time between subsequent QRS complexes (i.e., the time associated with a given HR) may also indicate a cardiac condition. In general, some variation in this component is normal and indicative of a healthy heart. Little or no variation, which typically becomes more pronounced as the patient ages, or a sudden decrease in variation, may indicate the onset of a cardiac event.

The QT interval, which is typically less than 50% of the total duration of the time associated with the patient's HR, represents the travel time of electrical activity through the patient's ventricles to the end of ventricular repolarization. This parameter varies with HR, and also with age and gender. Prolonged QT intervals represent a prolonged time to cardiac repolarization, and may indicate the onset of ventricular dysrhythmias.

The P-wave, which proceeds the QRS complex of each heartbeat, is typically upright and uniform in shape, and indicates the firing of the SA node and subsequent atrial depolarization; it typically has a width of about 50 ms, and an amplitude that is about 10-20% of the QRS amplitude. P waves that are abnormally wide or notched, or tall and peaked, indicate cardiac conditions such as P-mitrale and P-pulmonale, respectively. The PR segment, which separates this feature from the QRS complex, is typically 120-200 ms in duration, and represents the delay separating the firing of the SA node and ventricular depolarization. A PR segment that gradually increases over time may indicate the onset of damage to the patient's heart. The T-wave, which follows the QRS complex, indicates the onset of ventricular repolarization, and should appear rounded and somewhat symmetrical; the peak of the T-wave is typically relatively close to the wave's end. T-waves that are abnormally tall or 'tented' may indicate cardiac conditions such as hyperkalemia or myorcardial injury. T-waves that are inverted may indicate cardiac conditions such as myocardial ischemia, myocardial infarction, pericarditis, ventricular enlargement, bundle branch block, subarachnoid hemorrhage, and the presence of certain pharmaceutical compounds, such as quinidine or procainamide.

The U-wave, which is somewhat uncommon and when present only about 2-5% of the amplitude of the QRS complex, depicts the last phase of ventricular repolarization, it is typically present with patients undergoing bradycardia, and can be enlarged during cardiac conditions such as hypokalemia, cardiomyopathy, or enlargement of the left ventricle.

Figure 7:
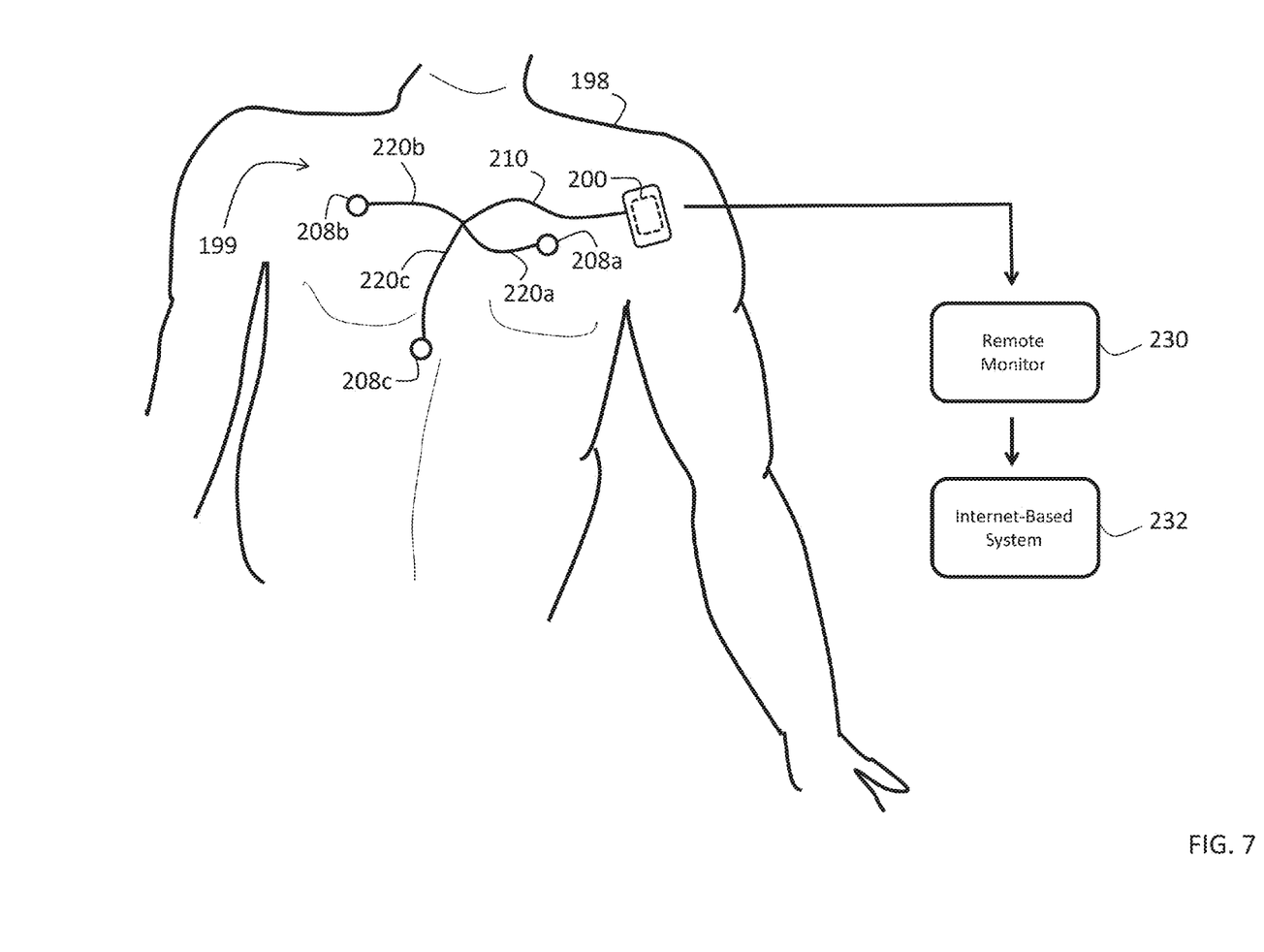
FIG. 7 shows a body-worn ECG monitoring system that measures ECG information and wirelessly transmits it to an Internet-based system associated with the system of FIG. 1.

FIG. 7 shows an example of a body-worn ECG monitoring system 199 according to the invention that continuously monitors ECO waveforms such as those shown in FIG. 4 from an ambulatory patient 198. The body-worn ECG monitoring system 199 features a control unit 200 that features analog electronics for measuring analog EGG waveforms, a processing unit for digitizing the analog ECG waveforms and then processing them as described above to determine HR and arrhythmia information, and a wireless transmitter for sending this information to a remote wireless monitor 230. During use, the control unit 200 connects to a cable 210 that, in turn, connects to a collection of ECG leads 220a-c. FIG. 7 shows a 3-lead system, but it is understood that the present invention could also include 5, 7, and 12-lead ECG systems. Each ECG lead 220a-c terminates with an ECG electrode 208a-c that adheres to the patient's skin and typically connects to the associated lead with a standard snap connector (not shown in the figure). In this case, the 3 ECG electrodes 208a-e are deployed on the patient's chest in a standard 'Einthoven's Triangle' configuration, meaning individual electrodes are attached to the upper left-hand (electrode 208a), upper right-hand (electrode 208b), and lower right-hand (electrode 208e) portions of the patient's torso. During use, the electrodes measure weak analog electrical signals from these locations, and transmit these through their respective leads 220a-c to the processing unit 200, which then processes the signals with the analog circuit to determine one or more analog ECG waveforms. An analog-to-digital converter than digitizes these and avails them to a microprocessor, which runs computer code corresponding to the beatpicker that picks out the appropriate features (e.g. the QRS complex corresponding to each heartbeat) and then analyzes them as described above. The processing unit then wirelessly transmits this and other information (e.g. digitized ECG waveforms) to the remote monitor 230. This system typically includes a computer server that connects through a wired connection to an Internet-based system 232, which in turn integrates with the system according to the invention, as shows schematically in FIG. 1. With this configuration, ECG waveforms measured before, during, and after the EP procedure can be collected and further analyzed by additional algorithm-based tools, such as that described with reference to FIG. 3, to evaluate the patient's cardiac performance.

Other embodiments to the ECG monitoring system 199 shown in FIG. 7, of course, are within the scope of the invention. For example, the system 199 can include additional physiological sensors, such as those that measure other vitals such as BP, RR, SpO2, and body temperature. The sensors can also measure physiological parameters that are not vital signs, such as stroke volume and cardiac output. In general, any physiological parameter (either numerical value or time-dependent waveform) can be measured with systems similar to those described above, and then stored in the database shown in FIG. 1 and analyzed with algorithm-based tools to characterize the patient.

Additionally, the body-worn monitor 199 described with reference to FIG. 6 can take many different forms. For example, the monitor 199 can connect to the remote monitor through a wired connection as opposed to a wireless one. The monitor 199 may also deploy body-worn sensors (e.g. the electrodes 208a-c) in configurations that are different, than those described above. The body-worn monitor 199 may also connect directly to the Internet-based system 232, thus bypassing the remote monitor. Different systems with different configurations may also be used to monitor the patient before, during, and after the EP procedure. All of these configurations are within the scope of the invention.

The above-mentioned system can be used to generate reports for the clinician that includes the following information:

1—physiological information before and after EP treatment
2—ECG waveforms and their various components before and after treatment
3—estimated efficacy of EP treatment
4—the need for EP treatment
5—correlation of patient demographies and EP efficacy
6—correlation of physiological information and EP efficacy Other embodiments are also within the scope of the invention. For example, other techniques besides the above-described algorithms can be used analyze data collected with the system. Additionally, processing units and probes for measuring ECG waveforms similar to those described above can be modified and worn on other portions of the patient's body. For example, the ECG-measuring system can be in a patch configuration. Or they can be modified to attach, to other sites that yield ECG waveforms, such as the back or arm. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit. In still other embodiments, the systems for measuring ECG waveforms are implanted or inserted in the patient, e.g. they are part of the AICD or EP system.

Systems similar to that described above can also be used for other cardiac procedures conducted in other areas of the hospital such as the catheterization laboratory, medical clinic, or vascular analysis laboratory. In these applications, data other than HR and ECG waveforms may be analyzed using techniques similar to those described above. Data used in these examples includes all vital signs, hemodynamic properties such as cardiac output and stroke volume, tissue perfusion, pH, hematocrit, and parameters determined with laboratory studies.

Still other embodiments are within the scope of the following claims.

What is claimed is:

1. A system for evaluating a patient, comprising:
a first ECG-measuring system connected to the patient and configured to sense ECG information;
a data-acquisition system interfaced to a vital sign-monitoring system connected to the patient, the vital-sign monitoring system configured to sense vital sign information during an electro-physiology (EP) procedure;
a software system interfaced to both the ECG-measuring system and the data-acquisition system, the software system comprising: i) a first software interface configured to receive ECG information sensed by the ECG-measuring system; ii) a second software interface configured to receive vital sign information from the data-acquisition system, the vital sign information sensed by the vital-sign monitoring system; a iii) a database configured to store ECG information sensed from the patient before and after the EP procedure, and vital sign information sensed from the patient during the EP procedure; and iv) an algorithm configured to evaluate the EP procedure by collectively analyzing at least two of the following: ECG information sensed from the patient before the EP procedure, ECG information sensed from the patient after the EP procedure, and vital sign information sensed from the patient during the EP procedure,
wherein the algorithm is configured to compare a first set of parameters extracted from ECG information sensed from the patient before the EP procedure to a second set of parameters extracted from ECG information sensed from the patient after the EP procedure and to determine the efficacy of the EP procedure, and wherein both the first set of parameters and the second set of parameters comprise arrhythmia information.

2. The system of claim 1, wherein the software system is interfaced to the Internet.

3. The system of claim 2, wherein the system further comprises a graphical user interface configured to render on a web browser.

4. The system of claim 1, further comprising a second ECG-measuring system.

5. The system of claim 4, wherein the first ECG-measuring system is configured to sense ECG information from the patient before the EP procedure, and the second ECG-measuring system is configured to sense ECG information from the patient after the EP procedure.

6. The system of claim 5, wherein both the first and second ECG-measuring systems are body-worn systems configured to be worn on the outside of the patient's body.

* * * * *